(12) United States Patent
De Meuter et al.

(10) Patent No.: US 8,088,411 B2
(45) Date of Patent: Jan. 3, 2012

(54) DIRECT COMPRESSIBLE TREHALOSE SOLIDS

(75) Inventors: Pascale Adolphine Emilienne De Meuter, Vilvoorde (BE); Hans Frederic Zoerb, River Falls, WI (US)

(73) Assignee: Cargill, Incorporated, Wayzata, MN (US)

( * ) Notice: Subject to any disclaimer, the term of this patent is extended or adjusted under 35 U.S.C. 154(b) by 1168 days.

(21) Appl. No.: 10/550,073

(22) PCT Filed: Mar. 22, 2004

(86) PCT No.: PCT/EP2004/002983
§ 371 (c)(1),
(2), (4) Date: Aug. 20, 2007

(87) PCT Pub. No.: WO2004/082576
PCT Pub. Date: Sep. 30, 2004

(65) Prior Publication Data
US 2008/0262106 A1    Oct. 23, 2008

(30) Foreign Application Priority Data
Mar. 21, 2003 (EP) .................................... 03006480

(51) Int. Cl.
*A61K 9/20* (2006.01)
*A61K 47/00* (2006.01)
*A01N 25/00* (2006.01)

(52) U.S. Cl. ................... 424/465; 424/464; 514/777
(58) Field of Classification Search .................. None
See application file for complete search history.

(56) References Cited

U.S. PATENT DOCUMENTS

| 5,441,644 A * | 8/1995 | Kinouchi ................. 210/651 |
| 5,958,455 A | 9/1999 | Roser et al. |
| 2002/0042393 A1 * | 4/2002 | Oobae et al. .................. 514/53 |
| 2002/0058101 A1 | 5/2002 | Ohashi et al. |

FOREIGN PATENT DOCUMENTS

| GB | 2 353 933 | 3/2001 |
| JP | 2001 213890 | 8/2001 |
| WO | WO 97/28788 | 8/1997 |

* cited by examiner

*Primary Examiner* — Ernst Arnold

(57) ABSTRACT

The present invention relates to direct compressible crystalline or semi-crystalline trehalose solids having a crystal form selected from the group consisting of trehalose dihydrate and mixtures of trehalose dihydrate and anhydrous trehalose, and having a specific surface area of at least 0.25 $m^2/g$ and products or tablets containing these. A process for preparing said solids comprises heating a solution of trehalose and applying shear and cooling. The trehalose solids can be applied in food, pharma and cosmetics and tablets prepared from said trehalose solids have improved tensile strength.

35 Claims, 4 Drawing Sheets

DIRECT COMPRESSIBLE TREHALOSE SOLIDS

TECHNICAL FIELD

The present invention relates to direct compressible crystalline or semi-crystalline trehalose solids and a process for preparing said solids and the application in tablets.

BACKGROUND OF THE INVENTION

Trehalose (α-D-glucopyranosyl-α-D-glucopyranoside) has been known from ancient times as non-reducing saccharide composed of two glucose molecules. It is found for example, in micro-organisms such as in fungi and in certain yeasts. It is also found in insects, mushrooms and in certain drought-resistant plants. It can be manufactured by fermentation with certain strains of yeast. Trehalose is sweet-tasting and has been suggested for use as a sweetener having reduced cariogenicity in chewing gum and the like. Furthermore, trehalose demonstrates satisfactory pH- and thermal-stabilities.

WO97/28788 describes tablets comprising a major fraction of trehalose as a diluent or excipient. The resulting tablets can be used as vehicles for oral administration of therapeutic substances. The tablets may be produced by direct compression.

GB 2,353,933 provides a sugar composition for tabletting by direct compression, comprising a minor fraction of particulate trehalose in combination with a major fraction of one or more substances that are not in themselves directly compressible to a sufficient extent for forming tablets having high integrity.

JP2001-213890-A relates to improvement of the fluidity of a trehalose and improving compression-molding properties by controlling the physical properties of trehalose.

There is a further need for having trehalose solids with improved compressibility properties.

The present invention provides such a product and a process for preparing it.

SUMMARY OF THE INVENTION

The present invention relates to crystalline or semi-crystalline trehalose solids characterized in that
a) Said solids have a specific surface area greater than 0.25 $m^2/g$, preferably greater than 0.30 $m^2/g$, more preferably a specific surface area of at least 0.40 $m^2/g$, and
b) Said solids contain a crystal form selected from the group consisting of trehalose dihydrate and mixtures of trehalose dihydrate and anhydrous trehalose.

The present invention relates to trehalose solids having an average particle size greater than 100 μm, preferably greater than 150 μm, preferably greater than 200 μm, more preferably greater than 250 μm.

Furthermore, the present invention relates to a process for preparing crystalline or semi-crystalline trehalose solids containing having a specific surface area greater than 0.25 $m/g^2$, preferably greater than 0.30 $m^2/g$, more preferably a specific surface area of at least 0.40 $m^2/g$, and containing a crystal form selected from the group consisting of trehalose dihydrate and mixtures of trehalose dihydrate and anhydrous trehalose and said process comprises the following steps:
a) Heating a solution of trehalose above its temperature of solubility,
b) Applying shear and cooling for obtaining trehalose solids, and
c) Optionally, drying the trehalose solids.

In particular, said solution of trehalose in step a) is an aqueous solution and is prepared from trehalose to which at least 5% water, based on dry substance of trehalose, is added. In addition, in said process the temperature of solubility is at least 80° C.

The trehalose solids of the present invention are used in food applications, feed, pharma applications, cosmetics, detergents, fertilizer or agrochemical products.

The present invention further relates to the use of said trehalose solids as cryoprotectant, as carrier, as binder in tablet formation or said solids are the integral part of the tablets.

The present invention relates to products for ingestion by humans or animals and containing the aforementioned crystalline or semi-crystalline trehalose solids.

The present invention further relates to products for detergents, cosmetics, fertilizers or agrochemicals and containing the aforementioned crystalline or semi-crystalline trehalose solids.

Furthermore, the present invention relates to tablets containing crystalline or semi-crystalline trehalose solids having a specific surface area greater than 0.25 $m^2/g$, and containing a crystal form selected from the group consisting of trehalose dihydrate and mixtures of trehalose dihydrate and anhydrous trehalose and wherein said tablets have a tensile strength of at least 4 $N/mm^2$, preferably of at least 6 $N/mm^2$, more preferably more than 7 $N/mm^2$.

DETAILED DESCRIPTION OF THE INVENTION

The present invention relates to crystalline or semi-crystalline trehalose solids characterized in that
a) Said solids have a specific surface area greater than 0.25 $m^2/g$, preferably greater than 0.30 $m^2/g$, more preferably a specific surface area of at least 0.40 $m^2/g$, and
b) Said solids contain a crystal form selected from the group consisting of trehalose dihydrate and mixtures of trehalose dihydrate and anhydrous trehalose. Trehalose solids having a specific surface area of 0.70 $m^2/g$ and more are obtainable.

The present invention can use α,α-trehalose, α,β-trehalose and β,β-trehalose as raw material. However, the naturally occurring α,α-trehalose is preferred.

Figure 4:
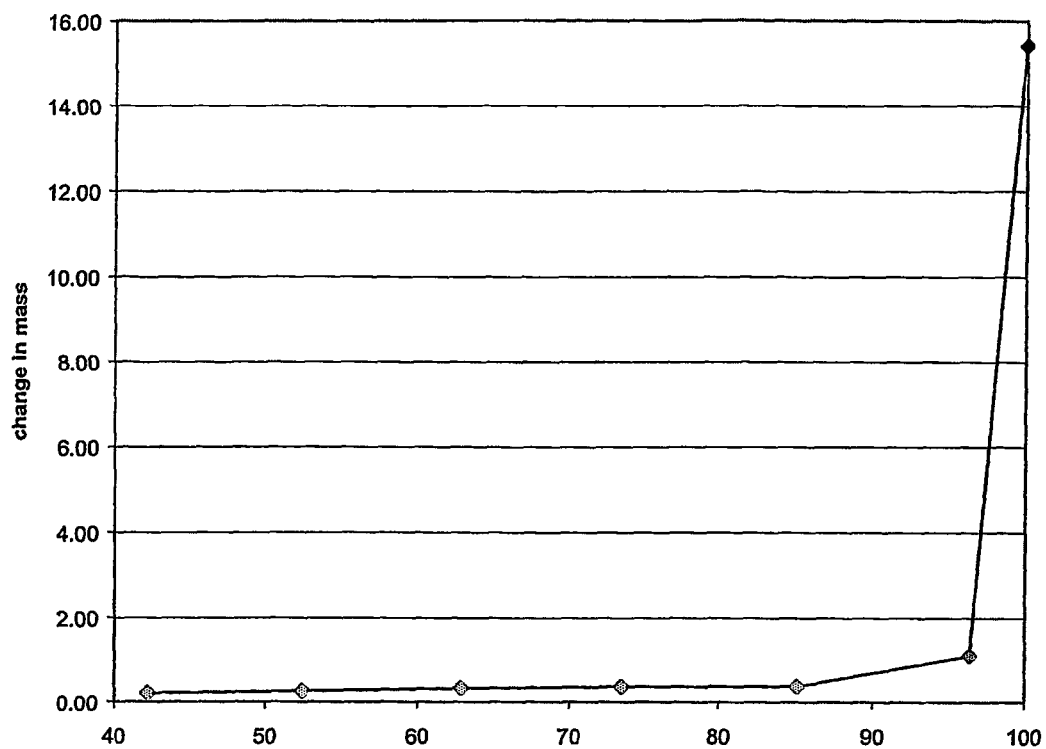
FIG. 4: graph of change in mass of trehalose solids in function of increasing relative humidity (%).

The trehalose solids in accordance with the invention exhibit a high specific surface area with nevertheless a low hygroscopicity. The low hygroscopicity is seen from the graph representing the change in mass of trehalose solids in function of relative humidity (see FIG. 4).

The trehalose solids of the present invention have much better properties than existing trehalose in solid form and these properties are due, at least in part to the particularly high specific surface area of this product.

The two crystal forms, that might be present in the solids, correspond to trehalose dihydrate and anhydrous trehalose. The ratio of trehalose dihydrate and anhydrous trehalose ranges from 100/0 to 10/90, preferably from 80/20 to 20/80 more preferably said ratio is from 60/40 to 40/60. Furthermore a ratio of trehalose dehydrate, and anhydrous trehalose of 50/50, or 45/55 is part of the present invention. The properties of these trehalose solids are significantly different from the properties of a traditional (physical) blend of trehalose dihydrate and anhydrous trehalose. The trehalose solids of the present invention benefit from a kind of synergistic effect resulting in superior properties such as direct compressibility, lower hygroscopicity than anhydrous trehalose, and improved flowability in comparison to amorphous trehalose.

The present invention relates to trehalose solids having an average particle size greater than 100 µm, preferably greater than 150 µm, preferably greater than 200 µm, more preferably greater than 250 µm. Actually, an average particle size of 275 µm and 300 µm can be reached. If the particle size is smaller than 100 µm the cohesion of the particles increases and the fluidity deteriorates. The trehalose solids of the present invention exhibit an excellent flow grade. The flowability of the powders is measured with the Flodex Powder Flowability Test instrument from Hanson Research of Chatsworth, Calif. The results are expressed as the diameter (in mm) of the hole through which three different samples of the same product flow freely in subsequent tests. This means the smaller the value the better the flow. According to this test Flodex flowability values of 30 and lower can be obtained.

The present invention relates to a process for preparing crystalline or semi-crystalline trehalose solids containing a crystal form selected from the group consisting of trehalose dihydrate and mixtures of trehalose dihydrate and anhydrous trehalose and, having a specific surface area greater than 0.25 m$^2$/g, preferably greater than 0.30 m$^2$/g, more preferably a specific surface area of at least 0.40 m$^2$/g, and said process is comprising the following steps:
  a) Heating a solution of trehalose above its temperature of solubility,
  d) Applying shear and cooling for obtaining trehalose solids, and
  b) Optionally drying the trehalose solids.

Temperature of solubility is the temperature at which there are no longer solid particles of trehalose in the solution, and the solution becomes transparent.

Trehalose can solubilise in any suitable polar solvent, preferably trehalose is solubilised in water. The aqueous solution can be prepared from trehalose to which at least 5% water, based on dry substance of trehalose, is added. Said trehalose can be trehalose dihydrate, anhydrous trehalose, or physical blends, or trehalose syrups. Preferably, trehalose dihydrate, anhydrous trehalose, physical blends are applied, since most of the time the purity of existing trehalose syrups is too low.

Such an aqueous solution, prepared from trehalose dihydrate, anhydrous trehalose or physical blends, has a temperature of solubility of at least 80° C.

During the heating of the solution of trehalose above temperature of solubility, the solution can be stirred to improve the heat transfer.

Applying shear is essential for obtaining trehalose solids containing a crystal form selected from the group consisting of trehalose dihydrate and mixtures of trehalose dihydrate and anhydrous trehalose and, having a specific surface area greater than 0.25 m$^2$/g, preferably greater than 0.30 m$^2$/g, more preferably a specific surface area of at least 0.40 m$^2$/g.

Optionally the trehalose solids are dried. Any type of dryer can be applied.

Furthermore, the present invention relates to the use of said trehalose solids in food applications, feed, pharma applications, cosmetics, detergents, fertilizer or agrochemical products. In fact, without being limiting, the trehalose solids of the present invention can be used in food products, animal feed, health food, dietetic products, animal medicine, with bath agent, in agrochemical products, with fertilizer, with plant granules, with plant seeds or seed grains, and any other product being it ingested by humans and/or animals or any other product which can benefit from the improved properties of the trehalose solids of the present invention.

In particular, the trehalose solids of the present invention can be used as cryoprotectant, as carrier, as binder in tablet formation or said trehalose solids can be tabletted as such without the addition of any excipient. Said tablets can be applied in food, feed, cosmetics, detergents and/or pharma applications. The trehalose solids of the present invention can be used as carrier for additives based on enzymes or microorganisms, detergent tablets, vitamins, flavors, perfumes, acids, sweeteners or various active ingredients with medicinal or non-medicinal applications. Eventually mixtures of additives can be applied.

The present invention relates to products for ingestion by humans or animals and containing the aforementioned crystalline or semi-crystalline trehalose solids. These products are further containing edible ingredients.

The present invention further relates to products for detergents, cosmetics, fertilizers or agrochemicals and containing the aforementioned crystalline or semi-crystalline trehalose solids. These products further contain ingredients suitable for the specific applications, e.g. detergents, cosmetics etc.

Furthermore, the present invention relates to tablets containing crystalline or semi-crystalline trehalose solids having a specific surface area greater than 0.25 m$^2$/g, preferably greater than 0.30 m$^2$/g, more preferably a specific surface area of at least 0.40 m$^2$/g and containing a crystal form selected from the group consisting of trehalose dihydrate and mixtures of trehalose dihydrate and anhydrous trehalose and wherein said tablets have a tensile strength of at least 4 N/mm$^2$, preferably of at least 5 N/mm$^2$, more preferably more than 7 N/mm$^2$. When necessary active ingredients can be added during the tabletting process. The solids of the present invention function as binder in the tablets and they can be used with or without any excipient.

Figure 2:
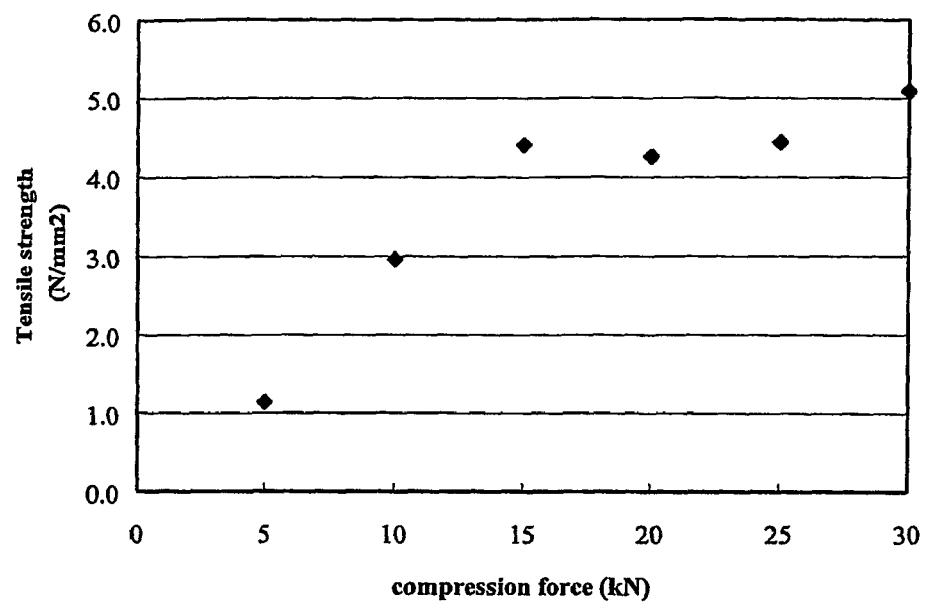
FIG. 2: graph with tensile strength of tablets prepared with trehalose solids. Tensile strength is expressed in function of increasing compression force.

The tensile strength of tablets can be expressed in function of compression force (see FIG. 2). A plateau is reached at 15 kN compression force. A tensile strength between 4 and 5 N/mm$^2$ is obtainable.

Because of its high compressibility, the mechanical strength of the tablets obtained with the trehalose solids of the present invention is indeed particularly high, in comparison with that of the tablets obtained with the commercial products. There is also a significant difference between the properties of the tablets prepared with the present disclosed trehalose solids and the properties of tablets prepared with physical blends of trehalose dihydrate and anhydrous trehalose (see comparative example).

As a lubricant agent in tablet formation, magnesium stearate, calcium stearate, stearic acid, sucrose fatty acid esters, and/or talc and the like can be applied.

The present invention has the following advantages:
Due to presence of a crystal form selected from the group consisting of trehalose dihydrate and mixtures of trehalose dihydrate and anhydrous trehalose, the trehalose

- solids are less hygroscopic than anhydrous trehalose and have improved storage stability.
- Trehalose solids of present invention show good flowability.
- Trehalose solids with such increased specific surface area are suitable for direct compressibility
- Tablets prepared from trehalose solids of present invention have excellent tensile strength properties The present invention is illustrated by way of the following examples.

EXAMPLE 1

Preparation of Trehalose Solids

Trehalose dihydrate (Treha® HS) was dissolved at 80% dry substance in hot water (90° C.) (taking into account the crystal water).

The aqueous solution was treated in pilot Readco extruder with the following operation parameters:
Speed of pump: 29 rpm
Speed of Readco: 50 rpm
Product feed: 53 kg/h
Inlet temperature: 99° C.
Outlet temperature: 38° C.
Cooling water inlet: 14° C.
Cooling water outlet: 23° C.

Crystallisation of the product was easy and the obtained strings or flakes were dried at 25° C. and 30% RH in a climate chamber. After drying the strings were broken, milled and sieved through a 500 μm sieve for obtaining trehalose solids. The ratio of trehalose dehydrate and anhydrous trehalose was 45/55.

Figure 1:
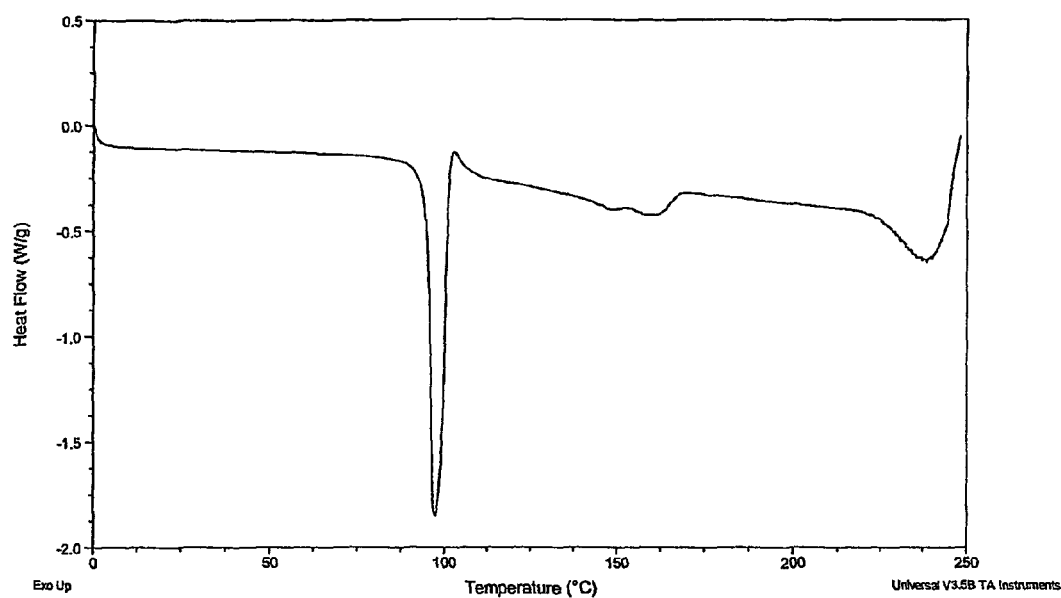
FIG. 1: DSC thermogram for trehalose solids comprising two crystal forms. The DSC thermogram (heating rate 5° C./min, hermetically closed DSC pan) shows that the material is completely crystalline (no Tg). Both dihydrate and anhydrous crystals are present.

Thermograms by DSC show the presence of two crystal forms (see FIG. 1). The melting of dihydrate crystals starts at 94° C. and is followed by the melting of anhydrous crystals. The melting point of anhydrous crystals is depressed by crystal water freed during melting of the dihydrate crystals since the DSC measurement was done in a hermetically closed DSC pan.

Further physico-chemical properties are displayed in Table 1. These physico-chemical properties have been measured according to the following methods:

Flowability

The flowability of the powders was measured with the Flodex Powder Flowability Test instrument. The results are expressed as the diameter of the hole through which three different samples of the same product flow freely in subsequent tests. This means the smaller the value the better the flow.

Moisture Content

The moisture content (including water of hydration) was determined using an IR balance. The sample was dried until the weight was stabilised. Approximately 2 g sample was used.

Particle Size

Particle size is determined with the Sympa TEC particle sizer based on laser diffraction. A representative sample passes through the laser beam and diffraction occurs. This diffraction pattern is detected by the photo-multiplier, which is linked to a PC giving the particle size profile of the sample. The average mean peak is reported. The value is expressed in μm.

Specific Surface

Specific surface of the samples was measured on a Gemini 2360.

9 $cm^3$ tubes were used. The reference tube was filled with glass beads The sample weight was approximately 5 g. Before the measurement the samples were flushed for 30 min with helium.

Density

The density was measured by weighing a full cup of 100 cc.

TABLE 1

| Density | $g/cm^3$ | 0.61 |
|---|---|---|
| Moisture (free and crystal water) | % | 9.1 |
| Specific surface | $m^2/g$ multiple | 0.32 |
| Flodex Flowability | mm | 30 |
| Average particle size | μm | 275 |

Tabletting

The milled and sieved product of the Readco treatment was applied for preparing tablets on the Fette tablettizer, (Type Perfecta 1000).

1% magnesium stearate based on dry substance of trehalose solids was added. The product was mixed for 3 minutes in a low shear rotating tubular mixer (Twist PBI 10975) and applied on the Fette tablettizer, and 22 punches were used.

The material was compressed at a speed of 20.000 tablets/h. The tablets had a diameter of 1.1 cm and a weight of 350 mg.

The properties of the prepared tablets were evaluated by measuring their tensile strength as a function of the compression force. The compression force was changed between 5 and 30 kN. The hardness was recalculated as tensile strength ($N/mm^2$) taking the dimensions of the tablets into account.

The tensile strength was measured with a Checkmaster (see FIG. 2).

In FIG. 2 the tensile strength of Readco extruded trehalose solids is depicted as a function of the compression force. A plateau value is reached at 15 kN compression force.

COMPARATIVE EXAMPLE

Physical Blends of Trehalose Dihydrate and Anhydrous Trehalose

A physical blend of 66% dihydrate (Treha® HS) and 33% anhydrous trehalose (HS) was made by mixing the two powders in a low shear rotating tubular mixer (Twist PBI 10975) for 10 min. The material had a specific surface area of 0.099 $m^2/g$.

After addition of 1% magnesium stearate based on dry substance of physical blend, the product was mixed for another 3 min.

350 mg tablets were made on a Fette tablettizer, using the same set-up as in example 1. The properties of the prepared tablets were evaluated by measuring their tensile strength as a function of the compression force.

Figure 3:
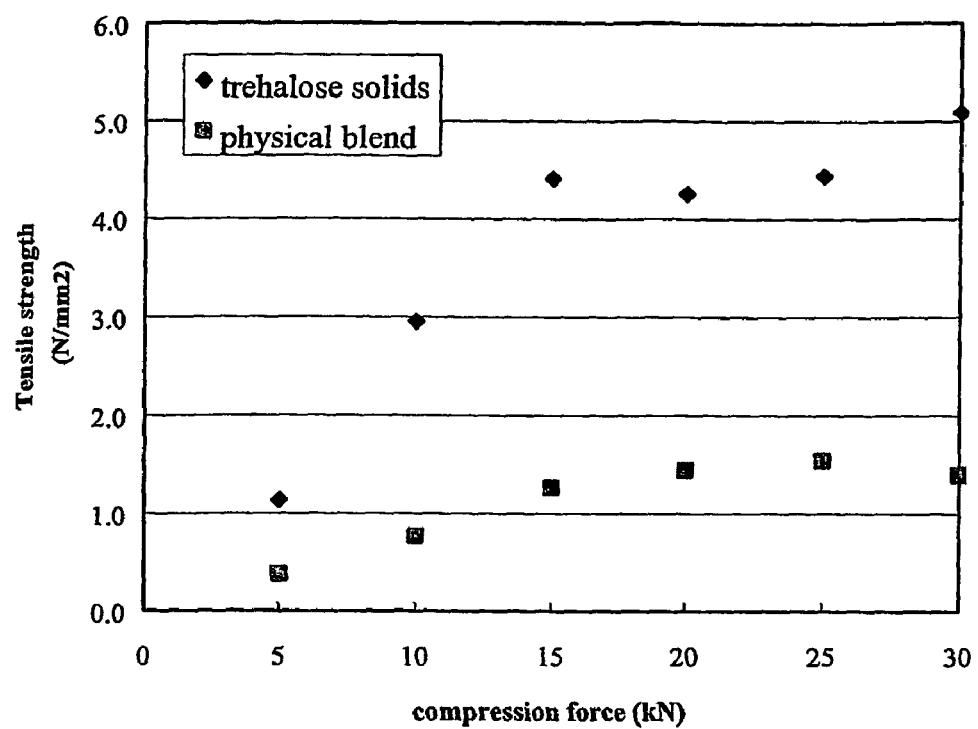
FIG. 3: graph with tensile strength of tablets prepared with trehalose solids and compared with tensile strength of tablets prepared with a physical blend of trehalose dihydrate and anhydrous trehalose (same ratio).

The tensile strength of tablets made from Readco extruded trehalose solids and tablets made from a physical blend of dihydrate and anhydrous trehalose crystals, were compared (see FIG. 3).

In FIG. 3 it is shown that the tensile strength of the tablets prepared with the physical blends is much lower than the tensile strength of the tablets prepared with the trehalose solids of the present invention.

The invention claimed is:

1. Crystalline or semi-crystalline trehalose solids, characterized in that the solids:
    a) have a specific surface area greater than 0.25 $m^2/g$, and b) comprise mixtures of trehalose dihydrate and at a ratio of 40/60 to 50/50 trehalose dihydrate/anhydrous trehalose.

2. The trehalose solids according to claim 1, characterized in that the solids have a specific surface area greater than 0.30 m$^2$/g.

3. The trehalose solids according to claim 1, characterized in that the solids have a specific surface area of at least 0.40 m$^2$/g.

4. The trehalose solids according to claim 1, characterized in that the solids have an average particle size greater than 100 µm.

5. The trehalose solids according to claim 4, characterized in that the solids have an average particle size greater than 150 µm.

6. The trehalose solids according to claim 4, characterized in that the solids have an average particle size greater than 200 µm.

7. The trehalose solids according to claim 4, characterized in that the solids have an average particle size greater than 250 µm.

8. A process for preparing crystalline or semi-crystalline trehalose solids, wherein the process comprises the following steps:
   a) heating a solution of trehalose above its temperature of solubility, wherein the trehalose comprises a mixture of trehalose dihydrate and at a ratio of 40/60 to 50/50 trehalose dihydrate/anhydrous trehalose,
   b) applying shear such that the sheared trehalose has a specific surface area greater than 0.25 m$^2$/g,
   c) cooling the sheared trehalose to obtain the trehalose solids, and
   c) optionally, drying the trehalose solids.

9. The process according to claim 8, wherein step b) comprises applying shear such that the sheared trehalose has a specific surface area of greater than 0.30 m$^2$/g.

10. The process according to claim 8, wherein step b) comprises applying shear such that the sheared trehalose has a specific surface area of at least 0.40 m$^2$/g.

11. The process according to claim 8, characterized in that the solution of trehalose in step a) is an aqueous solution.

12. The process according to claim 11, characterized in that the aqueous solution is prepared from trehalose and at least 5% water based on dry substance of trehalose.

13. The process according to claim 8, characterized in that the temperature of solubility is at least 80° C.

14. A food, feed, pharma, cosmetic, detergent, fertilizer or agrochemical product, comprising crystalline or semi-crystalline trehalose solids, wherein said trehalose solids comprise a mixture of trehalose dihydrate and at a ratio of 40/60 to 50/50 trehalose dihydrate/anhydrous trehalose, and wherein said trehalose solids have a specific surface area greater than 0.25 m$^2$/g.

15. The product according to claim 14, characterized in that said trehalose solids are applied as a cryoprotectant.

16. The product according to claim 14, characterized in that said trehalose solids are applied as a carrier.

17. The product according to claim 14, characterized in that said trehalose solids are applied as tablets or as binder in tablet formation.

18. The product according to claim 14, wherein said trehalose solids have a specific surface area greater than 0.30 m$^2$/g.

19. The product according to claim 14, wherein said trehalose solids have a specific surface area of at least 0.40 m$^2$/g.

20. The product according to claim 14, wherein said food or feed product is for ingestion by humans or animals.

21. A tablet comprising crystalline or semi-crystalline trehalose solids, wherein the trehalose solids comprise a mixture of trehalose dihydrate and at a ratio of 40/60 to 50/50 trehalose dihydrate/anhydrous trehalose, wherein the trehalose solids have a specific surface area greater than 0.25 m$^2$/g, and wherein the tablet has a tensile strength of at least 4 N/mm$^2$.

22. The tablet of claim 21, wherein the tablet has a tensile strength of at least 5 N/mm$^2$.

23. The tablet of claim 21, wherein the tablet has a tensile strength of more than 7 N/mm$^2$.

24. The trehalose solids according to claim 1, wherein the solids comprise mixtures of trehalose dihydrate and anhydrous trehalose at a ratio of 40/60 trehalose dihydrate/anhydrous trehalose.

25. The trehalose solids according to claim 1, wherein the solids comprise mixtures of trehalose dihydrate and anhydrous trehalose at a ratio of 45/55 trehalose dihydrate/anhydrous trehalose.

26. The trehalose solids according to claim 1, wherein the solids comprise mixtures of trehalose dihydrate and anhydrous trehalose at a ratio of 50/50 trehalose dihydrate/anhydrous trehalose.

27. The process according to claim 8, wherein the trehalose comprises a mixture of trehalose dihydrate and anhydrous trehalose at a ratio of 40/60 trehalose dihydrate/anhydrous trehalose.

28. The process according to claim 8, wherein the trehalose comprises a mixture of trehalose dihydrate and anhydrous trehalose at a ratio of 45/55 trehalose dihydrate/anhydrous trehalose.

29. The process according to claim 8, wherein the trehalose comprises a mixture of trehalose dihydrate and anhydrous trehalose at a ratio of 50/50 trehalose dihydrate/anhydrous trehalose.

30. The product according to claim 14, wherein the trehalose solids comprise a mixture of trehalose dihydrate and anhydrous trehalose at a ratio of 40/60 trehalose dihydrate/anhydrous trehalose.

31. The product according to claim 14, wherein the trehalose solids comprise a mixture of trehalose dihydrate and anhydrous trehalose at a ratio of 45/55 trehalose dihydrate/anhydrous trehalose.

32. The product according to claim 14, wherein the trehalose solids comprise a mixture of trehalose dihydrate and anhydrous trehalose at a ratio of 50/50 trehalose dihydrate/anhydrous trehalose.

33. The tablet of claim 21, wherein the trehalose solids comprise a mixture of trehalose dihydrate and anhydrous trehalose at a ratio of 40/60 trehalose dihydrate/anhydrous trehalose.

34. The tablet of claim 21, wherein the trehalose solids comprise a mixture of trehalose dihydrate and anhydrous trehalose at a ratio of 45/55 trehalose dihydrate/anhydrous trehalose.

35. The tablet of claim 21, wherein the trehalose solids comprise a mixture of trehalose dihydrate and anhydrous trehalose at a ratio of 50/50 trehalose dihydrate/anhydrous trehalose.

* * * * *